(12) United States Patent
Turner et al.

(10) Patent No.: US 9,327,046 B2
(45) Date of Patent: May 3, 2016

(54) DEVICE FOR EVAPORATING VOLATILE COMPOSITIONS

(71) Applicant: The Procter & Gamble Company, Cincinnati, OH (US)

(72) Inventors: Ronald David Turner, Walton, KY (US); Erik John Hasenoehrl, Loveland, OH (US); Jeannine Rebecca Bahm, Lebanon, OH (US); Dana Paul Gruenbacher, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 84 days.

(21) Appl. No.: 14/220,202

(22) Filed: Mar. 20, 2014

(65) Prior Publication Data

US 2014/0369895 A1     Dec. 18, 2014

Related U.S. Application Data

(60) Provisional application No. 61/834,619, filed on Jun. 13, 2013.

(51) Int. Cl.
*A61L 9/12* (2006.01)
*A01M 1/20* (2006.01)

(52) U.S. Cl.
CPC .............. *A61L 9/122* (2013.01); *A01M 1/2033* (2013.01); *A01M 1/2044* (2013.01); *A61L 9/127* (2013.01); *A61L 9/125* (2013.01); *A61L 2209/131* (2013.01); *A61L 2209/133* (2013.01)

(58) Field of Classification Search
CPC ............. A61L 9/00; A61L 9/02; A61L 9/032; A61L 9/04
USPC ...................................... 422/5, 306
See application file for complete search history.

(56) References Cited

U.S. PATENT DOCUMENTS

| | | | |
|---|---|---|---|
| 6,371,450 B1 | 4/2002 | Davis et al. | |
| 6,569,387 B1 * | 5/2003 | Furner et al. ................... | 422/123 |
| 7,498,369 B2 | 3/2009 | Whear et al. | |
| 7,648,127 B2 | 1/2010 | Cittadino | |
| 7,744,833 B2 | 6/2010 | Varanasi et al. | |
| 7,845,213 B2 | 12/2010 | Varanasi et al. | |
| 7,959,132 B2 | 6/2011 | Butler et al. | |
| 8,925,905 B2 | 1/2015 | Vieira | |
| 2010/0264232 A1 | 10/2010 | Gruenbacher et al. | |
| 2010/0308126 A1 | 12/2010 | Gruenbacher et al. | |
| 2010/0308130 A1 | 12/2010 | Gruenbacher et al. | |
| 2010/0314461 A1 | 12/2010 | Gruenbacher et al. | |
| 2011/0180621 A1 | 7/2011 | Gruenbacher et al. | |
| 2014/0091487 A1 | 4/2014 | Belongia | |
| 2014/0191056 A1 | 7/2014 | Gruenbacher et al. | |
| 2014/0197246 A1 | 7/2014 | Gruenbacher et al. | |
| 2014/0332990 A1 | 11/2014 | Brosmith | |

FOREIGN PATENT DOCUMENTS

EP     0 836 857 A1     4/1998

OTHER PUBLICATIONS

International Search Report for application No. PCT/US2014/042283, dated Nov. 18, 2014, containing 9 pages.

* cited by examiner

*Primary Examiner* — Monzer R Chorbaji
(74) *Attorney, Agent, or Firm* — Abbey A. Lopez; Amy I. Ahn-Roll

(57) ABSTRACT

A device comprises a delivery engine comprising a volatile composition and a microporous membrane, and an evaporation assistance element. In some embodiments the device includes a fan is configured to move a volume of air over the microporous membrane to facilitate evaporation of the volatile composition into the atmosphere.

24 Claims, 2 Drawing Sheets

DEVICE FOR EVAPORATING VOLATILE COMPOSITIONS

FIELD

Figure 1:
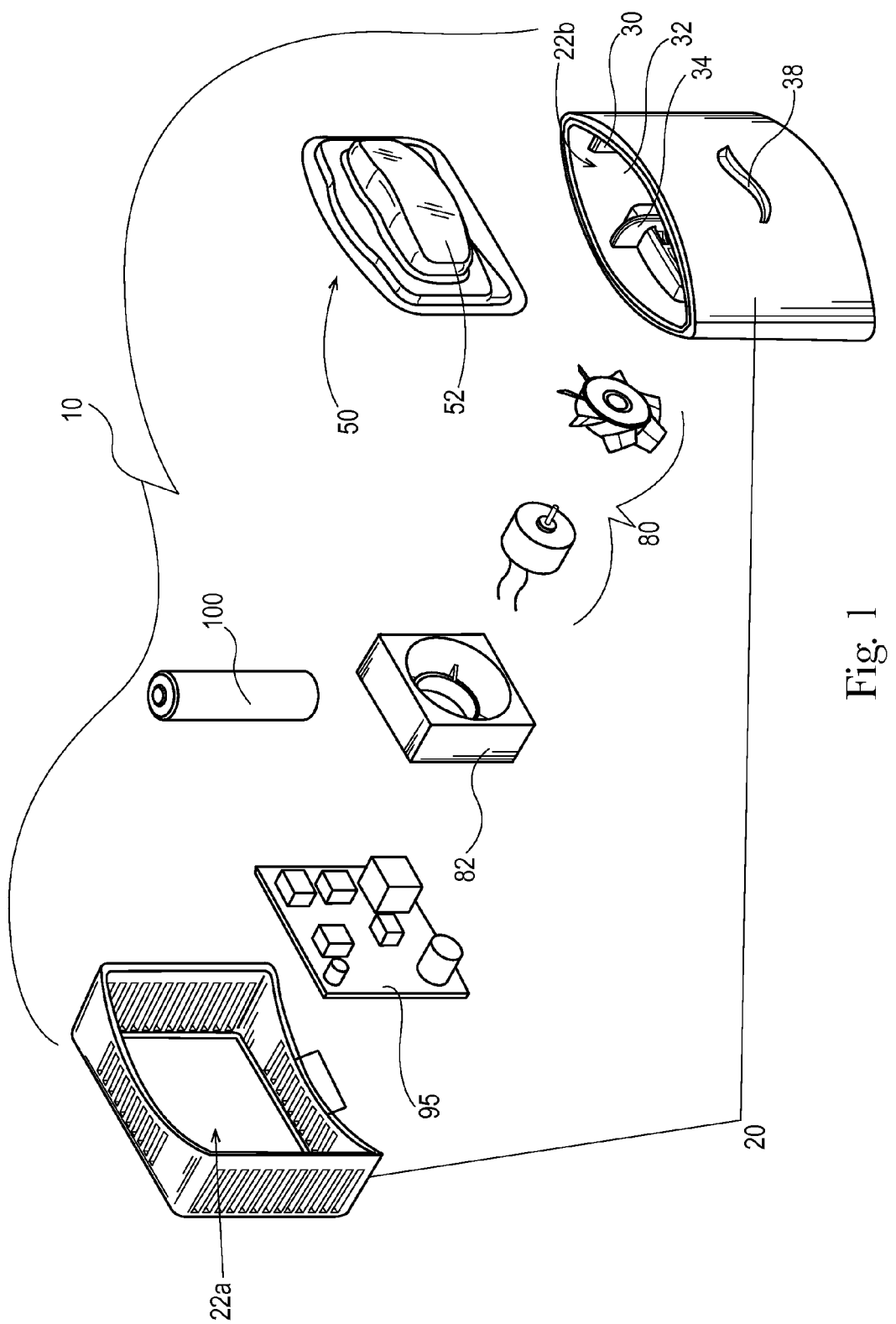
Figure 2:
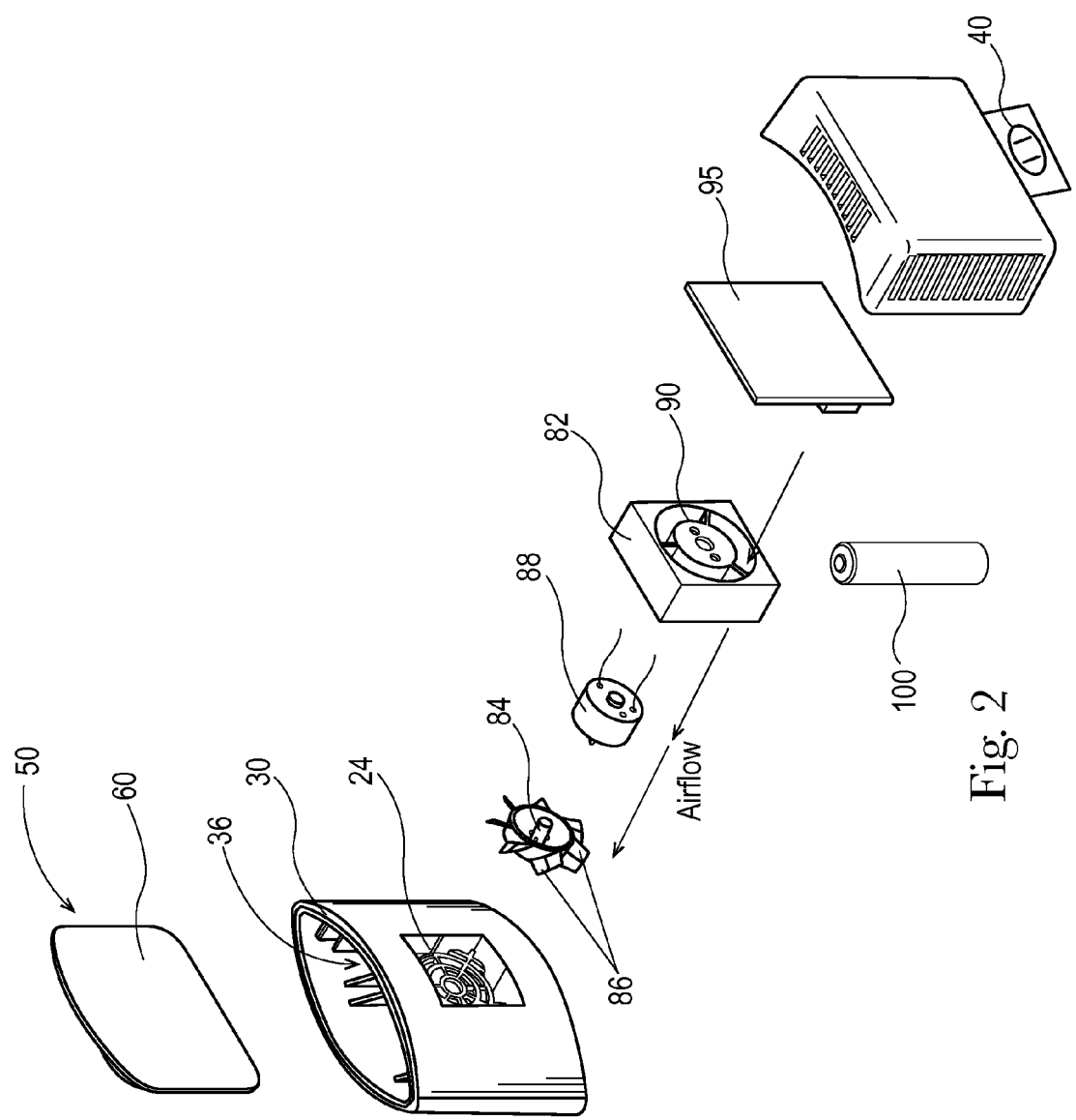

The present invention relates to a device for evaporating volatile compositions comprising a wicking substrate and an evaporation assistance element and methods thereof and, more particularly, relates to a device for evaporating liquid volatile compositions comprising a fan assembly and a microporous membrane.

BACKGROUND

Various devices in the marketplace provide a non-energized, continuous emission of a volatile composition (e.g. perfume or insecticide) to the atmosphere, whereby such emission plateaus and tapers off over time. Increasing the emission level of a volatile composition over its emission level in a non-energized state has been attempted with energized air freshening devices that include diffusion assistance means, such as heating elements, piezoelectric elements, and motorized fans. The addition of such diffusion assistance means in a device may require a larger amount of volatile composition, a larger device to accommodate the diffusion assistance means and/or the larger amount of composition, and, in turn, higher manufacturing and product cost. Further, another potential limitation of prior art devices is the wicking substrate which, often times, comprises membranes that limit the diffusion of certain types of volatile materials or comprises a porous substrate that may leak fluid when in certain orientations.

There remains a need for improved devices that emit volatile compositions into the atmosphere.

SUMMARY

According to one embodiment, there is provided a device comprising a housing; a fan assembly positioned within said housing; a delivery engine positioned within said housing and downstream of said fan assembly, wherein said delivery engine comprises a reservoir containing a liquid volatile composition, and a microporous membrane in fluid communication with said liquid volatile composition when said delivery engine is activated; and wherein said fan assembly is configured to move a volume of air at least partially over said microporous membrane to evaporate said liquid volatile composition into the atmosphere.

According to another embodiment, there is provided a device comprising a delivery engine comprising a reservoir containing a liquid volatile composition, and a microporous membrane in fluid communication with said liquid volatile composition when said delivery engine is activated; an evaporation assistance element configured to evaporate about 15 mg/hr to about 70 mg/hr of said liquid volatile composition from said microporous membrane into the atmosphere.

According to another embodiment, there is provided a device comprising a delivery engine comprising a reservoir containing a liquid volatile composition, and a microporous membrane in fluid communication with said liquid volatile composition when said delivery engine is activated, wherein said microporous membrane comprises an evaporation surface area of about 2 $cm^2$ to about 25 $cm^2$; and wherein said delivery engine comprises an evaporation rate of about 15 mg/hr to about 70 mg/hr of said liquid volatile composition from said microporous membrane into the atmosphere.

BRIEF DESCRIPTION OF DRAWINGS

The above-mentioned and other features and advantages of the present disclosure, and the manner of attaining them, will become more apparent and the present disclosure itself will be better understood by reference to the following description of various embodiments of the present disclosure taken in conjunction with the accompanying drawings, wherein:

FIG. 1 is an exploded front perspective view of a device in accordance with one embodiment.

FIG. 2 is an exploded rear perspective view of the device in FIG. 1.

DETAILED DESCRIPTION

Various embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting example embodiments and that the scope of the various embodiments of the present disclosure is defined solely by the claims. The features illustrated or described in connection with one example embodiment can be combined with the features of other example embodiments. Such modifications and variations are intended to be included within the scope of the present disclosure.

According to various embodiments, a device can be used to dispense a liquid volatile composition, such as a fragrance or an insecticide, to an area surrounding the device.

Referring to FIGS. 1 and 2, a device 10 in accordance with the present invention comprises a housing 20 comprising a delivery engine 50, which comprises a reservoir 52 containing a liquid volatile composition therein and a microporous membrane 60. The housing 20 also comprises a fan assembly 80.

Housing

The device 10 may comprise a housing 20 for housing the delivery engine 50 and the fan assembly 80. The housing 20 may be formed from a single part or from multiple parts that are joined together to define at least one chamber 22. The device shown in FIGS. 1 and 2 comprises a two-piece structure that is joined to form a first chamber **22*a* for housing the fan assembly 80 and a second chamber 22*b* for housing the delivery engine 50. In some embodiments, the housing defines a single chamber. The first chamber 22*a* and second chamber 22*b* are in air flow communication given a fan housing 82 is received by a fan port 24 in the second chamber 22*b*. Specifically, as shown in FIG. 1, air flows from the fan assembly 80 downstream to the delivery engine 50. "Downstream", as used herein, means a position in an airflow path that is later in time from a referenced position, when measuring air flow through a device. The housing 20 comprises one or more vents 38** for facilitating the passage of input air and output air into and out of the housing.

The housing is sized such that, when the fan assembly or evaporation assistance element is activated, from about 1 to about 20 air exchanges occur per second, or about 1 to about 10 air exchanges per second or about 5 to about 10 air exchanges per second. Where the fan assembly is programmed to operate 3 minutes in every hour (i.e. 5% duty cycle), for example, and where the fan assembly and housing 20 are configured to provide 10 air exchanges per second, 30 air exchanges may occur per minute during this duty cycle. In some embodiments, the chamber 22 volume ranges from about 2 cc to about 100 cc, or from about 5 cc to about 75 cc or from about 1 cc to about 25 cc.

The housing 20 may comprise at least one attachment member 30 configured to position and/or secure the delivery engine 50 in the housing 20. The attachment member 30 may align the edge of the delivery engine 50 with an inner wall of the housing 20 such that the delivery engine is slidably removable from the housing. Suitable attachment members also include a member that engages the delivery engine 50 by friction or compression; and/or a member comprising a magnetic connection.

In one embodiment, the housing 20 can comprise at least one projection 34 extending into the housing 20 from the inner wall 32. The at least one projection 34 can comprise pegs, ribs, posts, standoffs, elongate members, and/or pins, for example, which can serve to engage a portion of the delivery engine 50, maintaining the microporous membrane 60 at a distance away from the inner wall 32 of the housing 20. In some embodiments, the delivery engine 50 itself can comprise projections or like structures that extend therefrom to enable a surface of the microporous membrane 60 to be maintained at a distance away from the inner wall 32 of the housing 20. By maintaining the position of the microporous membrane 60 at a distance away from the inner wall 32, a gap 36 is formed intermediate the inner wall 32 and the microporous membrane 60. The gap 36 becomes at least partially saturated with the vapor phase of the liquid volatile composition as it evaporates out of the housing 20. The projection 34 may also assist the attachment member 30 in positioning the delivery engine 50 within the housing 20. In certain configurations where an impermeable rupturable substrate lies between the reservoir 52 and the microporous membrane 60, such as the embodiments disclosed in U.S. 2010/0308130A1 and U.S. 2010/0308126A1, the projection 34 may also assist with activating the delivery engine 50. More specifically, as the delivery engine 50 is inserted into the housing 20, the projection 34 presses into the microporous membrane 60, rupturing the rupturable substrate that lies beneath. In various embodiments, the one or more projections 34 can serve as baffles to direct air flow over the microporous membrane 60, maximizing air flow over the surface of the microporous membrane.

The housing 20 can also comprise a movable door (not shown) that can be opened to remove and/or replace the delivery engine 50. The housing 20 can also comprise a plug assembly 40 formed with the housing or in electrical communication with the housing, for example, by way of an electrical cord.

Delivery Engine

The device 10 of the present invention comprises a delivery engine 50 which comprises a reservoir 52 and a microporous membrane 60. Any reservoir or container that contains a liquid volatile composition and forms a fluid tight seal with the microporous membrane 60, in accordance with the present invention, may be used. The reservoir 52 can be thermoformed, injection molded, or blow molded with any known material including plastic, metal, or glass. In some embodiments, the reservoir 52 may be made of a multi layer material which may include a barrier layer to prevent evaporation of a volatile component and at least one outer sealant layer that allows a substrate to be heat-sealed, pressure sealed, ultrasonically sealed, and/or radio frequency sealed to the reservoir. A suitable sealant layer would include a layer of polyethylene or polypropylene or any suitable polyolefin sealant that allows for a leak proof seal of the reservoir 52. Suitable materials to form the reservoir 52 include plastics, such as Pentaplast Pentaform® 2101 available from Klockner. In some embodiments, the material is colored or non-colored see-through plastic. The see-through material permits observation of the liquid and end-of life.

The reservoir 52 may be elongate in that its width to length ratio is about 2:1 to 4:1, alternatively about 1.5:1 to about 2.5:1. The reservoir 52 may have a width of about 45 mm to about 55 mm, alternatively about 51 mm; a length of about 15 mm to about 30 mm to about, alternatively about 23 mm; a depth of about 5 mm to about 15 mm, alternatively about 11 mm. The dimensions of the reservoir 52 may be such that it holds about 1 ml to about 50 ml of a liquid volatile composition. Alternatively, the reservoir 52 may hold about 2 ml to about 30 ml, alternatively about 2 ml to about 10 ml, alternatively about 2 ml to about 8 ml, alternatively about 4 ml to about 6 ml, alternatively about 2 ml, alternatively about 6 ml of a liquid volatile composition.

It is contemplated that the present invention may comprise providing two or more reservoirs which can be filled with the same or different volatile materials. The reservoirs may have any configuration that is in fluid communication with the microporous membrane 60 when the device 10 is activated. For example, the reservoirs may be oppositely connected for use in a flippable device. In such a device the microporous membrane 60 is fluidly connected between the reservoirs.

The delivery engine 50 includes a microporous membrane 60 that is vapor permeable and capable of wicking liquid, yet prevents free flow of liquid out of the microporous membrane 60, thus addressing leakage problems. The microporous membrane 60 enables the diffusion of the volatile materials to be controlled by evaporation of the liquid volatile composition from the membrane versus being dependent on the diffusion rates of traditional polyethylene diffusion membranes.

The delivery engine 50 may include a rupturable substrate that prevents the volatile material in the reservoir 52 from contacting the microporous membrane 60 prior to activating or rupturing the delivery engine 50. The rupturable substrate 120 can be made of any material that ruptures with applied force, with or without the presence of an element to aid in such rupture.

The microporous membrane 60 may be secured to the delivery engine and encloses the reservoir 52 and the rupturable substrate if present. In this way, the rupturable substrate may be breached (without or without the presence of a rupture element) by compressing the microporous membrane 60. Once breached, the volatile composition flows out of the reservoir 52, contacts the microporous membrane 60, and is delivered to the atmosphere. Because the microporous membrane 60 is shielded from the volatile composition until the rupturable substrate is breached, the fragrance intensity may build slowly from zero to its equilibrium rate of release when the microporous membrane 60 is fully wetted.

The microporous membrane 60 of the present invention is capable of wicking a greater variety of perfume materials, leaving behind fewer perfume materials than traditional polyethylene diffusion membranes. Microporous membranes that are selective, such as traditional polyethylene films, may inhibit high molecular weight volatile materials and materials with low solubility in polyethylene from diffusing through. This may limit perfume formulations, for example in the field of air fresheners where it is typically desired to use formulations having a wide variety of volatile materials having different volatilities. For example, some microporous membranes made of traditional polyethylene films may preclude the diffusion of alcohols, such as linalool and dihydromyrcenol which are widely used in perfume applications.

While not wishing to be bound by theory, the physical characteristics of a microporous membrane may affect the evaporation rate of volatile materials through the microporous membrane. Such characteristics may include materials used, use of fillers, pore size, thickness, and evaporative surface area.

The microporous membrane 60 of the present invention may have an average pore size of about 0.01 to about 0.06 microns, alternatively from about 0.01 to about 0.05 microns, alternatively about 0.01 to about 0.04 microns, alternatively about 0.01 to about 0.03 microns, alternatively about 0.02 to about 0.04 microns, alternatively about 0.02 microns.

The microporous membrane 60 may be filled with any suitable filler and plasticizer known in the art. Fillers may include finely divided silica, clays, zeolites, carbonates, charcoals, and mixtures thereof. In one embodiment the microporous membrane 60 may be filled with about 50% to about 80%, by total weight, of silica, alternatively about 60% to about 80%, alternatively about 70% to about 80%, alternatively about 70% to about 75%.

The microporous membrane 60 may have a thickness of about 0.01 mm to about 1 mm, alternatively between about 0.1 mm to 0.4 mm, alternatively about 0.15 mm to about 0.35 mm, alternatively about 0.25 mm.

Those of ordinary skill in the art will appreciate that the evaporative surface area of the microporous membrane 60 can vary depending on the user preferred size of the delivery engine 50. In some embodiments, the evaporative surface area of the microporous membrane 60 may be about 2 $cm^2$ to about 100 $cm^2$, alternatively about 2 $cm^2$ to about 25 $cm^2$, alternatively about 10 $cm^2$ to about 50 $cm^2$, alternatively about 10 $cm^2$ to about 45 $cm^2$, alternatively about 10 $cm^2$ to about 35 $cm^2$, alternatively about 15 $cm^2$ to about 40 $cm^2$, alternatively about 15 $cm^2$ to about 35 $cm^2$, alternatively about 20 $cm^2$ to about 35 $cm^2$, alternatively about 30 $cm^2$ to about 35 $cm^2$, alternatively about 35 $cm^2$.

Suitable microporous membranes 60 for the present invention include a microporous, ultra-high molecular weight polyethylene (UHMWPE) optionally filled with silica as described in U.S. Pat. No. 7,498,369. Such UHMWPE microporous membranes include Daramic™ V5, available from Daramic, Solupor®, available from DSM (Netherlands), and Teslin™, available from PPG Industries, and combinations thereof. It is believed that these microporous membranes allow a volatile material to freely dissipate, while containing liquid within the delivery engine 50.

In one aspect of the invention, the microporous membrane 60 may include a dye that is sensitive to the amount of volatile material it is in contact with to indicate end-of-life. Alternatively, the microporous membrane 60 may change to transparent when in contact with a fragrance or volatile material to indicate diffusion is occurring. Other means for indicating end-of-life that are known in the art are contemplated for the present invention.

In certain embodiments, the liquid volatile composition can comprise a single chemical and/or a single material that is capable of entering the vapor phase or, more commonly, the liquid volatile composition can comprise a mixture of chemicals and/or materials that are capable of entering the vapor phase. In various embodiments, the liquid volatile composition can comprise substances that can function as air fresheners, deodorants, odor neutralizing materials, odor blocking materials, odor masking materials, aromatherapy materials, aromachology materials, essential oils, insecticides, pesticides, pheromones, medicinals, flavors and/or combinations thereof. In other various embodiments, the liquid volatile composition can comprise other materials that can act in their vapor phase to modify, enhance, and/or treat an atmosphere or an environment. The device 10 can be configured for use in any environment, such as a domestic environment, for example, and can be configured to dispense any suitable solutions, chemical, materials, and/or compositions.

A suitable delivery engine having a reservoir and microporous membrane and suitable liquid volatile compositions is described in US 2010/0308130A1 and US 2010/0308126A1.

In various embodiments, the device 10 can comprise any number of delivery engines, each engine comprising a different, slightly different, or the same liquid volatile composition. In other embodiments, the delivery engine 50 can comprise multiple chambers therein, each chamber comprising a different, slightly different, or the same liquid volatile composition. Each volatile composition can comprise a different, slightly different, or the same vapor pressure range, for example. This feature can be useful when a user wants to dispense a first dose amount of a first volatile composition and a second dose amount of a second volatile composition, for example. In an instance in which more than one volatile compound is within one container or chamber of a container, the volatile composition with the higher vapor pressure range may transform from a liquid phase into a vapor phase prior to the volatile composition with the lower vapor pressure range transforming into a vapor phase. In this circumstance, the volatile composition with the higher vapor pressure range would likely be dispensed first, while the volatile composition with the lower vapor pressure range would likely be dispensed second. In various embodiments, where different volatile compositions with different vapor pressure ranges are in separate delivery engines or chambers, the different volatile compositions can be dispensed from their respective containers simultaneously, for example. As a result, various volatile compositions can be dispensed from the device 10 to create a mixture of scents, for example, if the liquid volatile composition is a fragrance.

Fan Assembly

The fan assembly 80 can comprise any suitable fan or components configured to produce and/or intermittently move a volume of air into the fan inlet 90 and over the microporous membrane 60 of the delivery engine 50. While the specification describes the device 10 as including a fan assembly 80, it is contemplated that other evaporation assistance elements can be utilized to achieve improved evaporation of liquid volatile compositions from the delivery engine 50.

In one embodiment, the fan assembly 80 can be housed in a fan housing 82. In various embodiments, the fan assembly 80 can be positioned up to about 18 inches from the microporous membrane 60. The fan assembly 80 may comprises a rotatable hub 84, and at least two fan blades 86 extending from the rotatable hub or otherwise attached to or formed with the rotatable hub, and a motor 88.

The diameter of the rotatable hub 84 may be about 8 mm to about 20 mm. The drive shaft can be operably engaged with the rotatable hub 84 such that rotation of the drive shaft by the motor 88 rotates the rotatable hub and thereby rotates the at least two fan blades 86.

The motor 88 can provide continuous or intermittent movement of the fan blades 86 to provide a volume of air over the microporous membrane 60. In various embodiments, the fan assembly 80 may produce air speeds in the range of about 5 feet per minute to about 400 feet per minute or from about 50 feet per minute to 250 feet per minute. In one embodiment, the motor 88 can be a Mabuchi RF-J20WA-5Z145 motor that rotates the drive shaft at about 6200 revolutions per minute when 0.7 VDC is supplied to the motor 88 from the power source 100 and rotates the driveshaft at about 9400 revolutions per minute when 1.0 VDC is supplied to the motor 88 from the power source 100. In various embodiments, the flow rate of the volume of air generated by the motor 88 can be in the range of about 1.0 to about 8.0 mL/sec at about 0.7 VDC to about 6.0 to about 16.0 mL/sec at 1.0 VDC, depending upon the cross sectional area of the inlet orifice and the outlet orifice. By supplying various voltage levels to the motor 88, the rotational speed of the drive shaft and the resultant flow rate of the volume of air can be varied. Any other suitable motor can also be used with the fan assembly 80, such as a Sunon UB393-10 fan assembly, for example. Additionally, the controller 95 can supply the motor 88 with voltage using any suitable technique known to those of skill in the art. In various embodiments, a pulse width modulation technique can be used to provide voltage to the motor 88 over a specified range, such as about 0.7 VDC to about 1.0 VDC, for example. Additional circuitry or components, such as an analog-to-digital converter, can be used to compensate for various factors, such as the power source voltage and the ambient temperature, for example. In order to isolate or limit vibration due to the rotation of the drive shaft and/or the rotatable hub 84, vibration suppression devices or techniques can be used, such as silicon or thermoplastic elastomeric fan supports, for example, and/or the use of a gasket at the interface of the delivery engine 50 and the housing 20.

In one embodiment, the fan assembly 80 can comprises a centrifugal (i.e., radial) fan. Each fan blade 86 can comprise an air forcing surface that is positioned in a direction parallel to, or substantially parallel to, an axis of rotation of the rotatable hub. In one embodiment, an electrical current can be provided to the motor 88 via electrically conductive leads or terminal (not illustrated) to rotate the rotatable hub 84. Such rotation can cause a volume of air to be drawn into the fan inlet 90 and forced in a radial direction relative to the drive shaft. In other embodiments, the volume of air can be drawn from the atmosphere outside of the device 10 through any suitable vent or passageway on the housing 20, for example. The rotation of the at least two fan blades 86 can force the volume of air out of the fan housing 82 through the fan outlet and over the microporous membrane 60. In various embodiments, the at least two fan blades 86 can be arcuate, straight, and/or can have curved, straight, and/or arcuate portions. Additionally, the at least two fan blades 86 can have various cross-sectional shapes, such as an airfoil shape or a tapered shape, for example. As will be appreciated by those of skill in the art, after consideration of the present disclosure, a centrifugal fan can provide high efficiency with relatively small dimensions, and changes in pressure may have little influence on pressure head drops through the device 10.

In another embodiment, the fan assembly 80 can be an axial fan. This axial fan can comprise a rotatable hub 84 and at least three fan blades 86 extending from the rotatable hub. This at least three fan blades are attached to or formed with the rotatable hub. In one embodiment, the diameter of the rotatable hub 84 can be about 8 mm to about 20 mm, for example, although others dimensions could be possible. The fan assembly 80 can define a fan inlet 90. The drive shaft can be operably engaged with the rotatable hub 84 such that rotation of the drive shaft by the motor 88 rotates the rotatable hub and thereby rotates the at least three fan blades 86. In various embodiments, the fan assembly 80 may produce air speeds in the range of about 5 feet per minute to 400 feet per minute or alternatively from about 50 feet per minute to 250 feet per minute; although others air speeds could be possible.

Each blade 86 can comprise an air forcing surface that is positioned in a direction perpendicular to, or substantially perpendicular to, an axis of rotation of the rotatable hub. In one embodiment, an electrical current can be provided to the axial motor via electrically conductive leads or terminal (not illustrated) to rotate the rotatable hub 84. Such rotation can cause a volume of air to be drawn into the fan housing 82 through the fan inlet 90. With an axial fan configuration, the air flowing through the fan assembly 80 can be drawn through the fan inlet 90 and forced to move along the drive shaft direction. The rotation of the at least three fan blades 86 can force the volume of air out of the fan housing 82 through the fan outlet and over the microporous membrane 60. In various embodiments, the at least three fan blades 86 can be arcuate, straight, and/or can have curved, straight, and/or arcuate portions. Additionally, the at least three fan blades 86 can have various cross-sectional shapes, such as an airfoil shape or a tapered shape, for example. As will be appreciated by those of skill in the art, after consideration of the present disclosure, an axial fan can provide high efficiency with relatively small dimensions, and changes in pressure may have little influence on pressure head drops through the delivery engine 50.

Suitable fans for the present invention include a 30×30×6 mm MagLev Motor Fan (Model MC30060V1-000U-A99), supplied by Sunon Wealth Electric Machine Industry Co., Ltd of Taiwan; and fan model RF-330TK 07800, supplied by Mabuchi Motor. Another suitable fan for the present invention may have the following specifications:

Dimension: 120×120×25 mm
Fan Speed: 800~1500 rpm±250 RPM
Max Airflow: 66.55 CFM
Max Air Pressure: 1.42 mm H20
Bearing Type: Sleeve
Power: 5V The fan assembly 80 is powered by a power source 100 which may comprise a AC/DC outlet, a battery, such as a AA battery, a AAA battery, a 9-volt battery, rechargeable battery, and/or other suitable battery. In one embodiment, a solar power source, such as a solar cell, for example, can be used to power the device 10. In various embodiments, the solar cell (i.e., a photovoltaic cell) can be positioned on an outer portion of the device 10 or in communication with the device 10, such that the solar cell can receive light that can be transformed into energy to power the device 10. Those of skill in the art, upon review of the present disclosure, will recognize that any other suitable method or device can be used to provide power to the device 10.

In various embodiments, the control technique or approach for the fan 80 can be at least based on characteristics of the volatile composition. Volatile compositions with lower vapor pressures will likely evaporate slower than volatile compositions with higher vapor pressures. In various embodiments, the fan assembly 80 may not be activated until the microporous membrane 60 has reached full saturation or near full saturation of the volatile composition. In one embodiment, the deactivation time period of the fan 80 can be related to the time period necessary for the volatile composition to evaporate and saturate, or at least partially saturate, the space with the vapor phase volatile composition. In one embodiment, the activation time period of the fan assembly 80 can be related to the time period necessary to expel substantially all of the vapor phase volatile composition from the delivery engine 50 into the atmosphere. Once the vapor has been expelled from the delivery engine 50, the fan assembly 80 can be placed in an inactive state to again allow a portion of the volatile composition to enter the vapor phase.

By activating the fan assembly 80 for a period of time equal to, or approximately equal to, the amount to time necessary to expel at least most of the vapor phase volatile composition, the lifetime of the power source 90 can be optimized. Through control of the fan assembly 80, maximum vapor phase volatile composition release can be achieved with a minimum amount of fan assembly 80 running time. In various embodiments, the sequencing or pattern of activator actuation, or the flow rate of the volume of air produced by the fan assembly 80, can be adjusted to allow full or near full saturation of the volatile composition within the space for maximizing the vapor phase volatile composition release. In one embodiment, the fan assembly 80 can be activated for about 1 to about 10 seconds and then deactivated for about 1 to about 10 seconds, for example.

In various embodiments, the duration of activation of the fan assembly 80 or the flow rate of the volume of air provided by the fan assembly 80 can be increased to provide a higher intensity of volatile composition expulsion from the device 10. The fan assembly 80 can operate continuously or have intermittent operation. The fan assembly 80 may toggle on and off for a duty cycle of about 5% to about 50%, or from about 8% to about 20%. By providing a period of time between consecutive activations of the fan assembly, a user is more likely to notice a scent of the volatile composition again and avoid habituation.

Table 1 provides exemplary activation or toggling patterns of the fan assembly 80. As will be appreciated by those of skill in the art, a continuous operation of the fan and/or different pulsing frequencies and/or different air flow rates can be used to deliver different scent experiences.

TABLE 1

| Example Duty Cycles | Fan Active Time Period | Fan Inactive Time Period |
|---|---|---|
| High (50% duty cycle) (may be more efficient for volatile composition release but may use more power due to frequent activation and deactivation of the fan 80) | 10 sec. | 10 sec |
| High (50% duty cycle) (may be less efficient for volatile composition release but may not use as much power due to activation and deactivation of the fan 80) | 30 sec | 30 sec |
| High (50% duty cycle) (may be less efficient for volatile composition release but may not use as much power due to activation and deactivation of the fan 80) | 1 min | 1 min |
| High (50% duty cycle) (may be less efficient for volatile composition release but may not use as much power due to activation and deactivation of the fan 80) | 10 min | 10 min |
| Medium (20% duty cycle) | 10 sec | 40 sec |
| Medium (20% duty cycle) | 30 sec | 120 sec |
| Medium (20% duty cycle) | 90 sec | 360 sec |
| Medium (20% duty cycle) | 1 min | 4 min |
| Medium (20% duty cycle) | 3 min | 12 min |
| Medium (20% duty cycle) | 10 min | 40 min |
| Medium-Low (12.5% Duty Cycle) | 10 sec | 70 sec |
| Medium-Low (12.5% Duty Cycle) | 30 sec | 210 sec |
| Medium-Low (12.5% Duty Cycle) | 1 min | 7 min. |
| Medium-Low (12.5% Duty Cycle) | 3 min | 21 min |
| Low (10% duty cycle) | 10 sec | 90 sec |
| Low (10% duty cycle) | 20 sec | 180 sec |
| Low (10% duty cycle) | 1 min | 9 min |
| Low (10% duty cycle) | 4 min | 36 mins |
| Low (10% duty cycle) | 10 min | 90 min |
| Very Low (8% duty cycle) | 10 sec | 120 sec |
| Very Low (8% duty cycle) | 30 sec | 360 sec. |
| Very Low (8% duty cycle) | 1 min | 12 min |
| Very Low (8% duty cycle) | 3 min | 36 min |
| Ultra Low (5% duty cycle) | 5 sec | 95 sec |
| Ultra Low (5% duty cycle) | 10 sec | 190 sec |
| Ultra Low (5% duty cycle) | 20 sec | 380 sec |
| Ultra Low (5% duty cycle) | 1 min | 19 min |

In various embodiments, the evaporation rate of a liquid volatile composition from the device 10 can be about 5 mg/hr to about 75 mg/hr, or about 10 mg/hr to about 75 mg/hr, or about 15 mg/hr to about 70 mg/hr, or about 25 mg/hr to about 70 mg/hr, or about 25 mg/hr to about 60 mg/hr, or about 25 mg/hr to about 40 mg/hr.

It is contemplated that other evaporation assistance elements can be utilized to achieve the evaporation rate of a volatile composition from a device of the present invention. Such evaporation assistance element may include an agitation member or agitator, both powered agitator and manual agitator, to assist with agitating the liquid volatile composition in the reservoir. The evaporation assistance element may also include a heating element to heat the liquid volatile composition, a chemical constituent to speed evaporation or release rates, use of a chemically heated membrane to provide increased evaporation via exothermic reaction, or synergistic combinations thereof.

In various embodiments, a controller 95 may be positioned in electrical communication with the fan 80, such that the controller can instruct the fan 80 when to activate and which speed to rotate to force the volume of air over the microporous membrane 60. In one embodiment, the controller 95 can be any suitable type of controller, such as a microcontroller, for example. In one embodiment, the controller can be a Texas Instruments MSP430F2132 controller. In various embodiments, the controller 95 can comprise one or more user input buttons or switches configured to provide an input signal to the controller when depressed by a user, such that the controller can send corresponding output signals to the fan assembly 80 and/or the user feedback module, for example. In one embodiment, the various user input buttons or switches can comprise a power on/off switch configured to power on or power off the device 10 and at least one volatile composition dose amount button configured to allow the user to adjust the amount of volatile composition dispensed by the device 10. As will be appreciated, the input buttons or switches can be any combination of buttons and/or switches, such as push buttons, sliders, dials, knobs, for example.

In some embodiments, a communication network may be implemented to gather information about the device for the user. For example, the device may be configured with a central device controller to form ad hoc, wireless mesh networks and control multiple communication modules. For example, the central device controller may be in communication with sensors to sense the amount of a volatile composition that has evaporated into a room having the device. Other types of sensors may exist on the consumer product device 10.

In various embodiments, the amount of the liquid volatile composition dispensed over a predetermined time interval can be controlled by adjusting the rate at which the fan assembly 80 is activated by the controller (i.e., by adjusting the time period the fan 80 is active and the time period the fan 80 is inactive), by adjusting the speed at which the air is moved when the fan assembly 80 is active (i.e., by adjusting the rotational speed by adjusting the voltage to the motor 88), and/or by a combination of both techniques. In one embodiment, the device 10 can have a "boost" button for delivering a dose of the volatile composition to the atmosphere on demand. For example, if the boost button is depressed or otherwise activated, the fan assembly 80 can be activated for a specified time period, such as 30 to 60 seconds or at a specified rotational speed, for example.

In various embodiments, the controller 95 can also be in electrical communication with a temperature sensor configured to sense the temperature of the atmosphere. In various embodiments, the temperature sensor can send a signal to the controller 95 indicative of the temperature of the space, such that the controller can provide an output signal to the fan assembly 80 or other various components of the device 10, indicative of a volatile composition dosing amount for a particular temperature and/or temperature range. For example, higher temperature ranges may require greater dose amounts than lower temperature ranges to achieve the desired result. As a result, the device 10 can be power efficient such that it can maximize the life of the power source 100. The device 10 can be activated for 1-30 seconds, for example, and then be inactive for 10-200 seconds, for example. In other various embodiments, the device 10 can be set by a user to provide a desired intermittent dosing amount.

In various embodiments, the device 10 can comprise a sensor, such as a visible indicator, a light source, and/or an audible alert, configured to provide feedback to the user regarding the status of the device 10. In one embodiment, the sensor can be used to alert the user of a property of the device 10. In such embodiments, the feedback can be visual and/or audible and can indicate to the user, among other things, whether the device 10 is powered on, what volatile composition dosing amount is being dispensed, the power level of the power source 100, the amount, type, or level of the volatile composition within the delivery engine 50, and/or any other suitable feedback helpful or beneficial to the user. In various embodiments, the sensor can comprise one or more one indicators, such as a plurality of light sources, for example, electrically coupled to the controller and/or to the power source 100, and a translucent portion in the housing 20, such that the one or more indicators can be viewed by the user though the housing 20. In one embodiment, the one or more indicators can be oriented in any suitable fashion such that various lights of the one or more indicators can emit visible light through the translucent portion of the housing 20, depending on what type of feedback is being provided to the user. In one embodiment, the translucent portion of the housing 20 can comprise any suitable shape and the one or more indicators can be arranged in a similar shape so that as one indicator, such as a light source, for example, is powered or unpowered, the user is provided with a first feedback and, as two or more light sources are powered or unpowered, the user is provided with at least a second feedback and so forth. In one embodiment, at least one button is at least partially translucent allowing for one or more indicators to be viewable through the button.

With some liquid volatile compositions (for instance those comprising fragrances) it may be helpful to adjust the fan speed, frequency of run time, or on/off time to compensate for the changing volatile composition formulation as high vapor pressure volatile composition raw materials will evaporate more quickly than low vapor pressure raw materials. In this case it may optionally be desirable to have the controller operate the fan more frequently as the volatile composition is evaporated over a period of many days. For instance in one non-limiting example, the fan could run at 10% duty cycle for the first 10 days of usage but then slowly increase up to about 30% to about 40% duty cycle from days 11 up to 60 days. In this way, the fan frequency or duration can be increased to compensate for potentially a decline in fragrance intensity. By adjusting for the age, it is possible to deliver a more consistent scent intensity even as the fragrance amount and mixture of high to low vapor pressure components is changing with time. One non-limiting example of a means of keeping track of run time of the delivery engine 50 is to monitor the voltage of the battery associated with the delivery engine 50. For instance, a new AA battery may be 1.60 Volts to about 1.65 Volts while a AA battery that was used for thirty days might have a voltage of about 1.2 Volts to about 1.45 Volts. By monitoring the voltage of the battery, the controller 95 can recognize the life of the delivery engine 50 and can adjust operating conditions to deliver a consistent scent experience over the life of the delivery engine 50.

Another non-limiting example of a means to monitor time, is to start a timer when the delivery engine 50 is inserted and to keep track of hours/minutes that the fan has operated. As mentioned above, the fan time could be adjusted as the product ages to deliver a more consistent scent experience.

In the instance where the battery voltage or run time is viewed as the indicator of the full life of the delivery engine 50, the controller could be programmed to provide a signal to the user such as turning on a red light or provide a flashing light to indicate that the delivery engine 50 is empty and/or needs to be replaced.

Methods

The present disclosure also includes a method of evaporating a liquid volatile composition into a space. The method may comprise the step of providing a device having a fan assembly or an evaporation assistance element and a delivery engine, where the delivery engine has a liquid volatile composition therein and a microporous membrane in fluid communication with the liquid volatile composition. The method includes activating via a power source the fan assembly or an evaporation assistance element. In some embodiments, where the evaporation assistance element includes chemistry or an agitator, the activation step may include adding effective amounts of the chemical evaporation assistance element or manual agitation of the device and/or delivery engine to assist with evaporating the liquid volatile composition. The method of the present invention also includes activating the fan assembly or evaporation assistance element according to a duty cycles as disclosed herein.

EXAMPLES

A Glade® "Décor Scents" refill and a Febreze® "Set and Refresh" refill were activated, per instruction on package, and placed in a Febreze Set & Refresh housing and was allowed to sit at room temperature for a period of 1 hour to equilibrate to room conditions. After one hour, the device and refill were weighed and placed at 2.5 cm, 15 cm, and 30 cm from the front of the Thermaltake™ USB fan with the fan operating continuously for a period of 1 hour at either low or high setting. The specification of the fan used is reported below:
 Dimension: 120×120×25 mm
 Fan Speed: 800~1500 rpm±250 RPM
 Max Airflow: 66.55 CFM
 Max Air Pressure: 1.42 mm H20
 Bearing type: Sleeve
 Power: 5V The air flow velocity is reported in Table 2 for both low and high settings and can be determined by the following calculation:

$$\text{Air Velocity} = 1096.2 * (Pv/D)^{(1/2)}$$

Wherein:
D=Air Density=1.325*(Pb/T);
Pb=Barometric Pressure in inches of Mercury;
T=Absolute Temperature (Farenheit degrees+460); and
Pv=Velocity Pressure in "inches of water"*.
*note 0.004016 inches of water=1 Pa (N/m^2)
Example Calculations:

$$\text{Barometric Pressure} = 30.12 \text{ mm Hg} = Pb$$

$$\text{Temperature} = 75° F. \; (\text{Absolute } Temp = 460 + 75° F. = 535) = T$$

$$\text{Air Pressure, measured in Pascals, using Pitot Tube} = 1.01 \text{ Pa}$$

$$Pv \text{ (inches of Water)} = Pv \text{ (Pascals)} * 0.004016$$

$$Pv = 1.01 * 0.004016 = 0.00405616 \text{ inches of water.}$$

$$\begin{aligned}
\text{Air Velocity} &= 1096.2 * (Pv/D)^{\wedge}(1/2) \\
&= 1096.2 * (0.004056/(1.325 * (Pb/T))^{\wedge}(1/2) \\
&= 1096.2 * (0.00405616/(1.325 * (30.12/535)))^{\wedge}(1/2) \\
&= 1096.2 * (0.00405616/(1.325 * (0.056299)))^{\wedge}(1/2) \\
&= 1096.2 * (0.00405616/(0.074596))^{\wedge}(1/2) \\
&= 1096.2 * (0.054376)^{\wedge}(1/2) \\
&= 1096.2 * (0.23318) \\
&= 255.62 \text{ ft/min.}
\end{aligned}$$

TABLE 2

| | | No Fan | Fan @ 1" HI 402'/Min. | Fan @ 1" LOW 263'/Min. | Fan @ 6" HIGH 202'/Min. | Fan @ 6" LOW 76'/Min. | Fan @ 12" HIGH 150'/Min. | Fan @ 12" LOW 25'/Min. |
|---|---|---|---|---|---|---|---|---|
| Glade "Décor Scents" | Evaporation Rate (mg/hr) | 9 | 11 | 9 | 11 | 9 | 11 | 9 |
| Test device | Evaporation Rate (mg/hr) | 8 | 60 | 44 | 43 | 30 | 35 | 27 |

Table 2 shows that a device according to the present invention, on low and on high settings, evaporates more liquid volatile composition from the microporous membrane into the air with a fan assembly than without a fan assembly; while a device having PE (i.e. lacking a microporous membrane) does not have the same level of improved evaporation and, in many cases, the same diffusion levels with and without a fan.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A device comprising:
    a housing;
    a fan assembly positioned within said housing;
    a delivery engine positioned within said housing and downstream of said fan assembly, wherein said delivery engine comprises:
        a reservoir containing a liquid volatile composition, and
        a microporous membrane in fluid communication with said liquid volatile composition when said delivery engine is activated; and
    wherein said fan assembly is configured to move a volume of air at least partially over said microporous membrane to evaporate said liquid volatile composition into the atmosphere,
    wherein said microporous membrane comprises an evaporative surface area of about 2 cm$^2$ to about 100 cm$^2$.

2. The device of claim 1 wherein said microporous membrane comprises an average pore size of about 0.01 to about 0.03 microns.

3. The device of claim 1, wherein said microporous membrane comprises an average pore size of about 0.02 microns.

4. The device of claim 1, wherein said microporous membrane comprises an evaporative surface area of about 2 cm$^2$ to about 25 cm$^2$.

5. The device of claim 1, wherein said liquid volatile composition comprises about 40% to about 100%, by total weight, of volatile materials each having a vapor pressure, at 25° C., of less than about 0.1 torr.

6. The device of claim 1, wherein said liquid volatile composition comprises about 50%, by total weight, of volatile materials each having a vapor pressure, at 25° C., of less than about 0.1 torr.

7. The device of claim 1, wherein said liquid volatile composition comprises:
    a. 0% to about 15%, by total weight, of volatile materials each having a VP at 25° C. of about 0.004 torr to about 0.035 torr;
    b. about 0% to about 25%, by total weight, of volatile materials each having a VP at 25° C. of about 0.1 torr to about 0.325 torr; and
    c. about 65% to about 100%, by total weight, of volatile materials each having a VP at 25° C. of about 0.035 torr to about 0.1 torr.

8. The device of claim 1, wherein said liquid volatile composition comprises a viscosity of about 1.0 cP to less than about 15 cP.

9. The device of claim 1, wherein said liquid volatile composition comprises a surface tension of about 19 mN/m to less than about 27 mN/m.

10. The device of claim 1, wherein said volatile material mixture comprises a perfume material.

11. The device of claim 1, wherein said microporous membrane is positioned downstream of said fan assembly and said microporous membrane is spaced at a maximum distance of about 2 cm to about 45 cm from said fan assembly.

12. The device of claim 1, wherein said housing comprises an inner wall, wherein said microporous membrane and said inner wall define a gap, said gap is from about 0.5 mm to about 3 mm.

13. The device of claim 1, wherein said housing further comprises a plug assembly.

14. The device of claim 1, comprising a sensor configured to sense a property of the device and an indicator configured to alert a user of said property.

15. A device comprising:
   a delivery engine comprising:
      a reservoir containing a liquid volatile composition, and
      a microporous membrane in fluid communication with said liquid volatile composition when said delivery engine is activated;
   an evaporation assistance element configured to evaporate about 15 mg/hr to about 70 mg/hr of said liquid volatile composition from said microporous membrane into the atmosphere,
      wherein said microporous membrane comprises silica.

16. The device of claim 15 wherein said evaporation assistance element is a fan configured to evaporate about 25 mg/hr to about 70 mg/hr of said liquid volatile composition from said microporous membrane into the atmosphere.

17. The device of claim 15 wherein said microporous membrane comprises an average pore size of about 0.01 to about 0.03 microns.

18. The device of claim 15, wherein said microporous membrane comprises an evaporative surface area of about 2 $cm^2$ to about 25 $cm^2$.

19. The device of claim 15, wherein said liquid volatile composition comprises about 40% to about 100%, by total weight, of volatile materials each having a vapor pressure, at 25° C., of less than about 0.1 torr.

20. The device of claim 15, wherein said liquid volatile composition comprises about 50%, by total weight, of volatile materials each having a vapor pressure, at 25° C., of less than about 0.1 torr.

21. The device of claim 15, wherein said liquid volatile composition comprises a viscosity of about 1.0 cP to less than about 15 cP.

22. The device of claim 15, wherein said liquid volatile composition comprises a surface tension of about 19 mN/m to less than about 27 mN/m.

23. The device of claim 15, wherein the device comprises a housing, wherein said delivery engine and said evaporative assistance element are position in said housing.

24. A device comprising:
   a delivery engine comprising:
      a reservoir containing a liquid volatile composition, and
      a microporous membrane in fluid communication with said liquid volatile composition when said delivery engine is activated, wherein said microporous membrane comprises an evaporation surface area of about 2 $cm^2$ to about 25 $cm^2$; and
   wherein said delivery engine comprises an evaporation rate of about 15 mg/hr to about 70 mg/hr of said liquid volatile composition from said microporous membrane to the atmosphere.

* * * * *